United States Patent [19]

Napoli

[11] 4,196,323
[45] Apr. 1, 1980

[54] COMBINED INPUT CONNECTOR AND LEAD SELECTION SWITCH FOR ELECTRICAL SIGNAL PROCESSING APPARATUS

[75] Inventor: Joseph D. Napoli, Billerica, Mass.
[73] Assignee: American Optical Corporation, Southbridge, Mass.
[21] Appl. No.: 833,933
[22] Filed: Sep. 16, 1977
[51] Int. Cl.² .............................................. H01H 9/02
[52] U.S. Cl. ............................ 200/51.04; 200/51.05; 200/51.08; 200/51.09
[58] Field of Search .............. 200/51.03, 51.04, 51.05, 200/51.06, 51.07, 51.08, 51.09, 51.16, 51 R

[56] References Cited

U.S. PATENT DOCUMENTS

| | | | |
|---|---|---|---|
| 2,857,570 | 10/1958 | Simpson | 200/51.07 |
| 3,222,471 | 12/1965 | Steinkamp | 200/51.07 |
| 3,766,351 | 10/1973 | Cryer | 200/51 |

FOREIGN PATENT DOCUMENTS

| | | | |
|---|---|---|---|
| 263699 | 11/1965 | Australia | 200/51 R |
| 1337940 | 8/1963 | France | 200/51 R |

*Primary Examiner*—Joseph Man-Fu Moy
*Attorney, Agent, or Firm*—Jeremiah J. Duggan; Howard R. Berkenstock, Jr.; Stephen A. Schneeberger

[57] ABSTRACT

A consolidated input connector-selector switch and calibration switch for a medical instrument wherein the input connector and switch is mounted in the medical instrument housing partially in registry with an opening through the panel thereof. The selector switch is a multi-position rotary switch of a plurality of input and output terminals rotatable through a discrete number of positions. The switch is adapted to receive a connector having a plurality of signal leads and is operably connected with through drive means with the selector switch by rotation of the input connector rotates the selector switch. Additionally, the combination connector-selector switch is movable between forward and rearward positions being preferably biased forwardly and coupled with calibration switch means such that axial movement of the connector-selector switch combination actuates the calibration function within the medical instrument.

17 Claims, 14 Drawing Figures

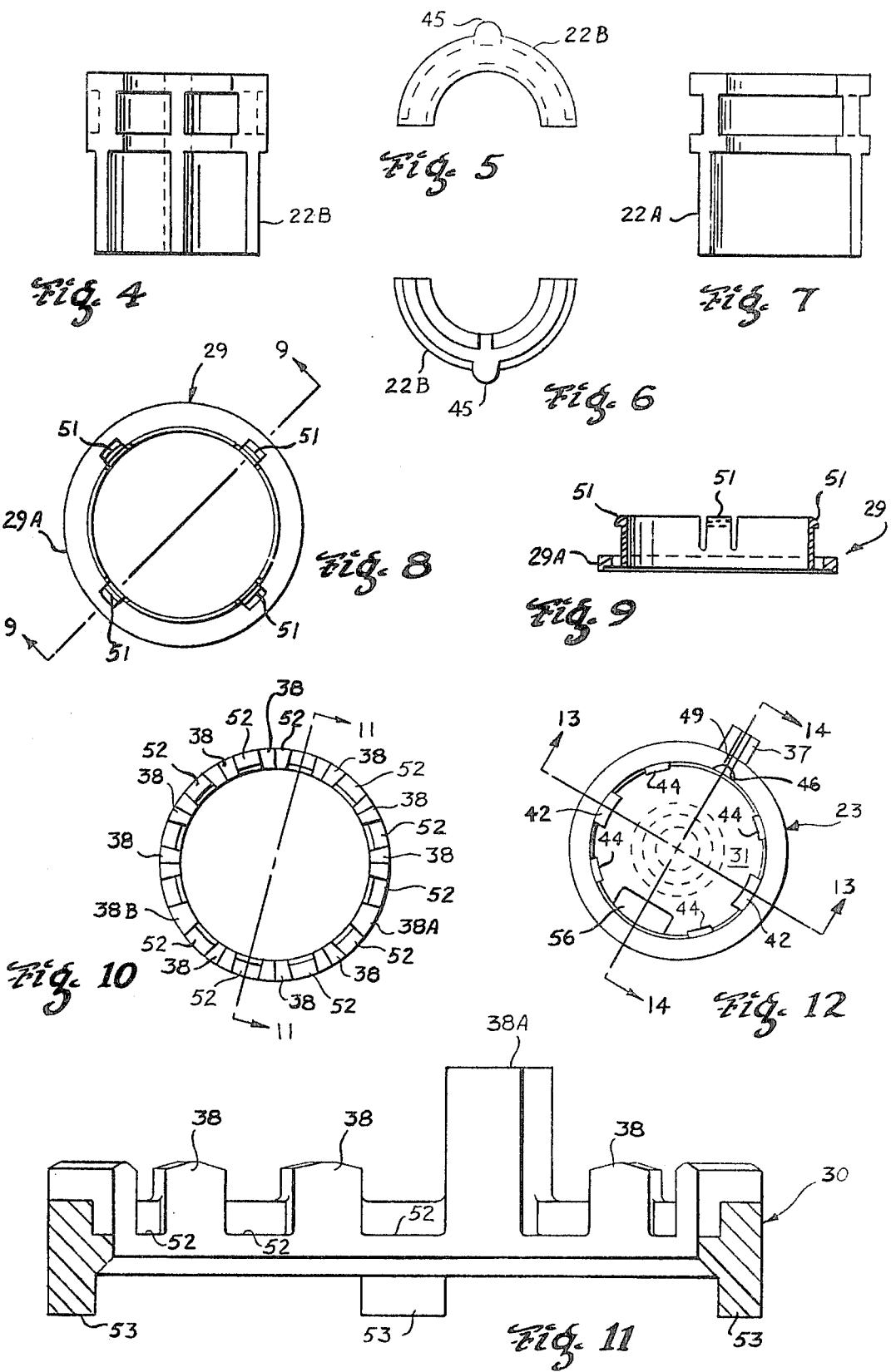

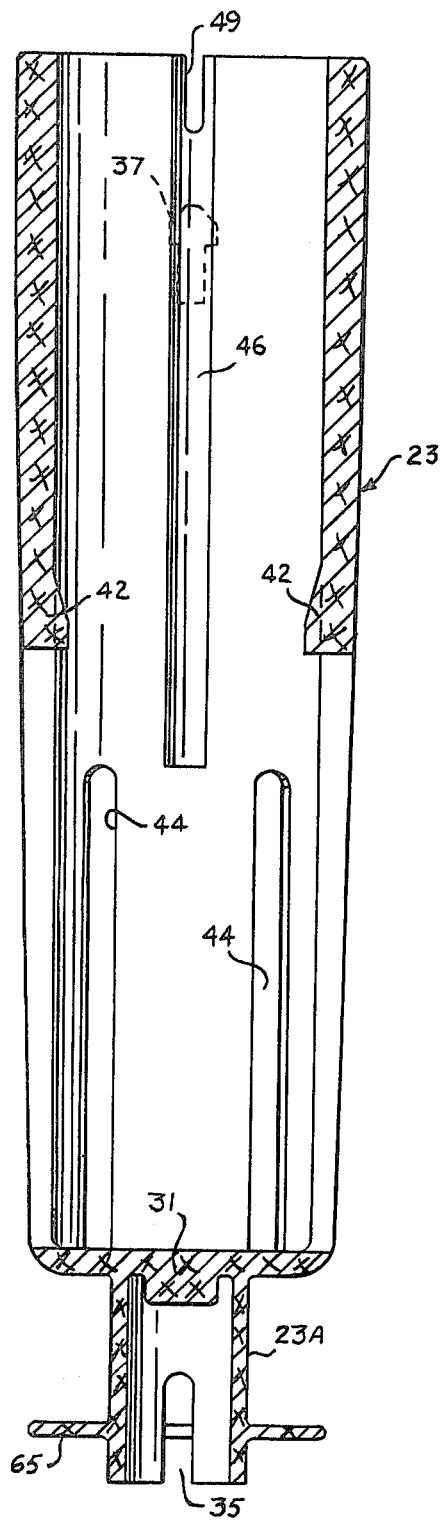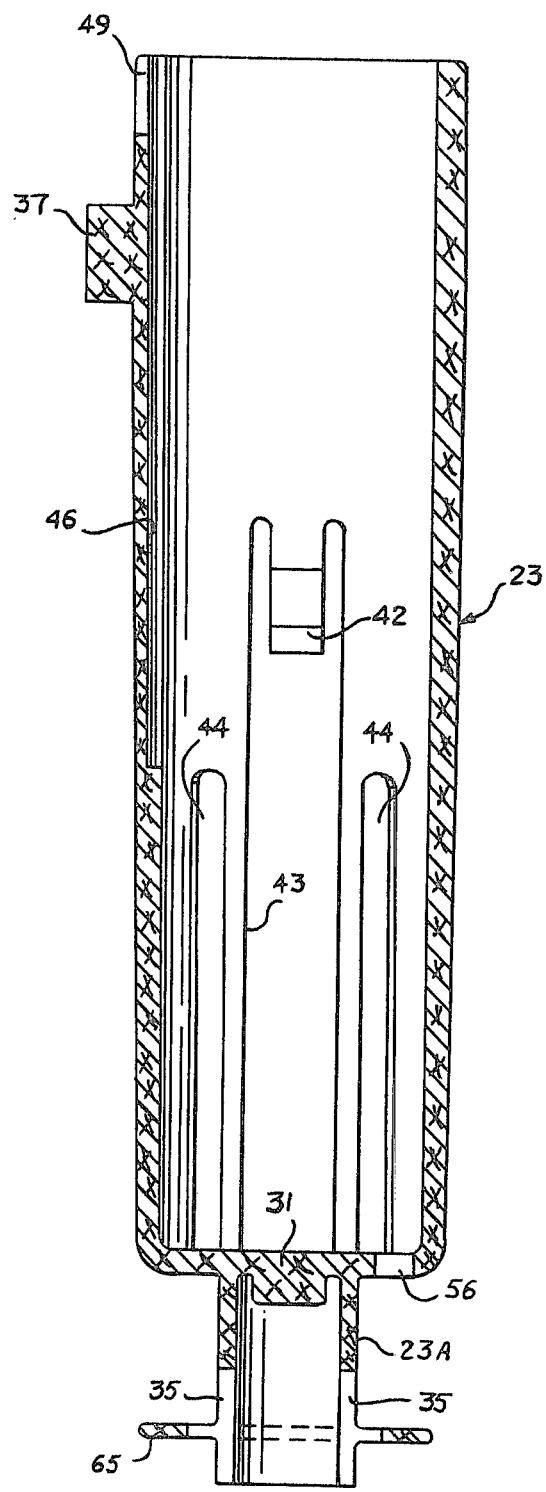

COMBINED INPUT CONNECTOR AND LEAD SELECTION SWITCH FOR ELECTRICAL SIGNAL PROCESSING APPARATUS

BACKGROUND OF THE INVENTION

The invention relates generally to apparatus for switchably connecting electrical input signals to electrical signal processing apparatus. More particularly, the invention relates to a combined input and lead selection switch, useful for electrical signal input to signal processing apparatus, and adapted for connection with a first-half of a multi-contact connector for plural input signal leads.

In a number of electrical signal processing applications, it is known to connect plural input signals to the signal processing apparatus via conventional connector means and additionally to employ a selector switch electrically connected with the various input signal leads for selecting which one or more of the incoming signals will be passed on to the signal processing apparatus. One particularly significant application is that of connecting biological signals (e.g. electrical signals from the heart) with appropriate signal processing apparatus, as for instance heart signal amplifiers and their electrocardiographic display means. Normally, one half (i.e. the receptacle) of a multi-contact connector has been mounted in the face panel of the signal processing apparatus for receiving connection with the other connector half (i.e. plug) which contains plural signal leads from the respective plural electrodes applied to the chest, arm and/or leg of the patient. A manually operated selector switch also mounted on the apparatus panel adjacent the input connector has permitted the selection of various pairs of input signal leads for relay of the signal developed thereacross to the signal processing apparatus. Still further, such types of electrical signal processing apparatus have often included an additional switch also mounted on the front panel thereof adjacent the input connector and the selector switch for the further purpose of providing a calibration standard when actuated.

While such an arrangement of multi-lead input connector and selector switch, and possibly also a calibration switch or the like, has generally been satisfactory, it has required the use of a significant amount of front panel space. However, with increased minaturization of electronic components, the electrical packaging has also decreased in size with an attendant reduction in the front panel surface area. Furthermore, as additional functions have been required of a particular electronic signal processing apparatus, additional control switches and/or indicator lights have been added to the front panel to provide for such added functions. Either or both of the foregoing conditions have led to a situation of "crowding" amongst the input connector indicator lights and/or control switches occupying the front panel of the apparatus.

In the particular situation of electrical signal processing apparatus associated with monitoring biological functions, it is becoming increasing important to provide electrical isolation between the input signal leads and initial circuitry connected to the patient and that remaining circuitry utilized for the bulk of the signal processing. Such electrical isolation is in part for the protection of the circuitry and more importantly, for the protection of the patient connected to the input leads. In heart signal processing apparatus, such isolation may include the connector for the input signals, the lead selector switch, the calibration switch if present and a preamplifier. In the event the input lead connector, the lead selector switch, and the calibration switch require separate locations on the front panel of the apparatus the task of isolating and shielding these portions of the circuit from the remainder of the circuitry may be particularly cumbersome and require that excessive amount of space within the apparatus package.

Applicant and his attorney are unaware of any prior art pretaining specifically to a combined multi-lead input connector and lead selection switch mounted in the housing for signal processing apparatus. A search of the switch art revealed the following four U.S. Patents which are concerned with plug and switch combinations, though of a type and/or application different than contemplated in the present instance:

U.S. Pat. Nos. 2,480,787; 2,752,465; 2,787,676 and 2,797,559. The Kellog et al and the Stephan U.S. Pat. Nos. 2,787,676 and 2,480,787 respectively, both relate to a combination electric plug and switch of the type associated with an electrical power cord. The combination is not normally mounted in signal processing apparatus housing and is only capable of switching power on and off.

The MacDonald U.S. Pat. No. 2,752,465 relates to a combination locking push button and adjustment knob, however, there is no provision for extending multiple leads to the switch via an input connector combined therewith particularly for the purpose of actuating the switch.

The Maberry U.S. Pat. No. 2,797,559 discloses a plug connector reversing switch having plural inputs. However, to change connections (conductive paths) the plug must be withdrawn and repositioned.

Accordingly, it is a principal object of the present invention to provide a multi-contact input connector and lead selection switch which reduce the front panel surface area requirement.

It is another principal object of the present invention to provide a signal lead input connector and a lead selection switch configured and positioned to facilitate the electrical isolation thereof.

It is further an object of the present invention to apply the foregoing objectives to a calibration switch or the like in addition to an input connector and a lead selection switch.

It is another object of the invention to provide a lead selector switch and a calibration switch or the like which are conveniently actuated with a minimum of manual control.

These and other objects of the invention will be in part obvious and in part pointed out in greater detail hereinafter.

SUMMARY OF THE INVENTION

In accordance with the present invention there is provided, for electrical signal input to signal processing apparatus having a housing and including a panel, a consolidated or combined input connector and lead selection switch adapted for receiving connection with a first-half of a multi-contact connector for plural input signal leads. The combined input connector and lead selection switch is mounted in the signal processing apparatus housing at least partially in registry with an opening through the panel thereof and comprises a multi-position rotary switch having a plurality of input terminals, at least one output terminal and an input shaft, the switch input shaft being rotatable to plural discreet positions for respectively changing the connection between the switch input terminals and the at least one switch output terminals, the switch being adapted to the substantially fixedly mounted in the apparatus housing; a second half of the multi-contact connector adapted to removedly receive the first half of the multi-contact connector to provide electrical connection with the plural input signal leads; electrical conductor means for connecting the contact of the second half of the multi-contact connector with respective ones of the switch input terminals; connector-receiving means mounted in the apparatus housing in registry with the opening in the apparatus panel for retainedly housing and second half of the multi-contact connector and for detented rotation to plural selected angular position about an axis of rotation extending substantially normal to the apparatus panel; and drive means connecting and connector-receiving means with the input shaft of the rotary switch whereby the selective rotation of the connector-receiving means is operative to selectively change the connection between the switch input terminals and the at least one switch output terminal.

More particularly, the combination input connector and lead selection switch comprises a substantially rigid shaft member extending rearwardly from the apparatus panel into the interior of the apparatus housing. The shaft is axially hollow at its forwad end for retaining the multi-contact connector second half therewithin. Means such as keys and key ways, coact between the multi-contact connector second half and the connector-receiving means to prevent relative rotation therebetween whereby rotation of the connector second half is operative to actuate the rotary switch. The multi-contact connector second half is preferably contained within a multipiece housing or shell in nonrotating relationship therewith, the shell in turn being releasably retained within the connector-receiving means in substantially fixed relationship therewith. The axial restraint of the multipiece housing within the shaft member is provided by resilient locking finger means which extend radially inwardly from the inside diameter of the shaft member into axially retaining engagement with a shoulder of the multipiece housing.

The shaft member selectively movable normally of the apparatus panel between forward and rearward positions, and biasing means operatively coact between the shaft member and the apparatus housing for urging the shaft member to the forward position. Conveniently, the biasing means may be a spring unit posed in compression between the drive means and the shaft member. A first detent member comprising a casillated locking ring is mounted on the panel in coaxially encircling relationship with the shaft member. A second detent member is mounted on the shaft member against angular displacement relative thereto and the shaft member is axially slidable relative to the locking ring. The shaft member is detented when the second detent member thereon is urged forwardly with the shaft member into one of the interdental spaces between adjoining castillations on the locking ring. The shaft member and accordingly, the selection switch, may be rotated by urging the shaft member rearwardly out of detented engagement with the locking ring and subsequently applying the requisite rotary motion. Certain castellations at opposite ends of a predetermined angular range may extend rearwardly at sufficient length to walk further rotation of the shaft member even in its rearward position.

The combination input connector and lead selection switch may additionally be utilized for actuating additional switch means. For instance, the shaft member may be provided with an annular flange or actuator ring affixed thereto and a linearly actuated calibration switch or the like may be fixedly positioned for actuation by contact with the actuator ring when the shaft member is moved to its rearward position. Furthermore, the actuator ring is slightly yieldable in the axial direction to prevent applying excessive force to the actuator member of the calibration switch.

DESCRIPTION OF THE DRAWINGS

FIG. 4 is a plan view of one half of connector shell used in the invention;

FIG. 5 is a rear view of the connector shell of FIG. 4;

FIG. 6 is a front view of the connector shell of FIG. 4;

FIG. 7 is a plan view of the other half of the connector shell;

FIG. 8 is a rear view of the connector bezel of the invention;

FIG. 9 is a sectional view of the connector bezel taken along line 9—9 of FIG. 8;

FIG. 10 is a rear view of the locking ring of the invention;

FIG. 11 is a sectional view of the locking ring taken along line 11—11 of FIG. 10;

FIG. 12 is a front end view of the connector shaft of the invention;

FIG. 13 is a longitudinal section of the connector shaft taken along line 13—13 of FIG. 12; and FIG. 14 is a longitudinal section of the connector shaft taken along line 14—14 fo FIG. 12.

DESCRIPTION OF A PREFERRED EMBODIMENT

Figure 1:
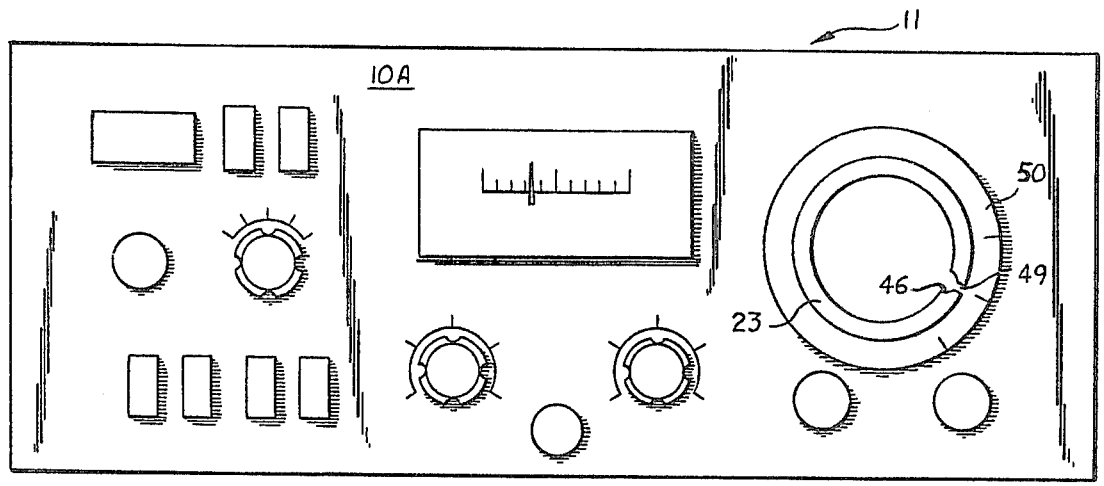
FIG. 1 is a view of the front panel of signal processing apparatus incorporating the combination input connector and lead selection switch of the invention.
Figure 2:
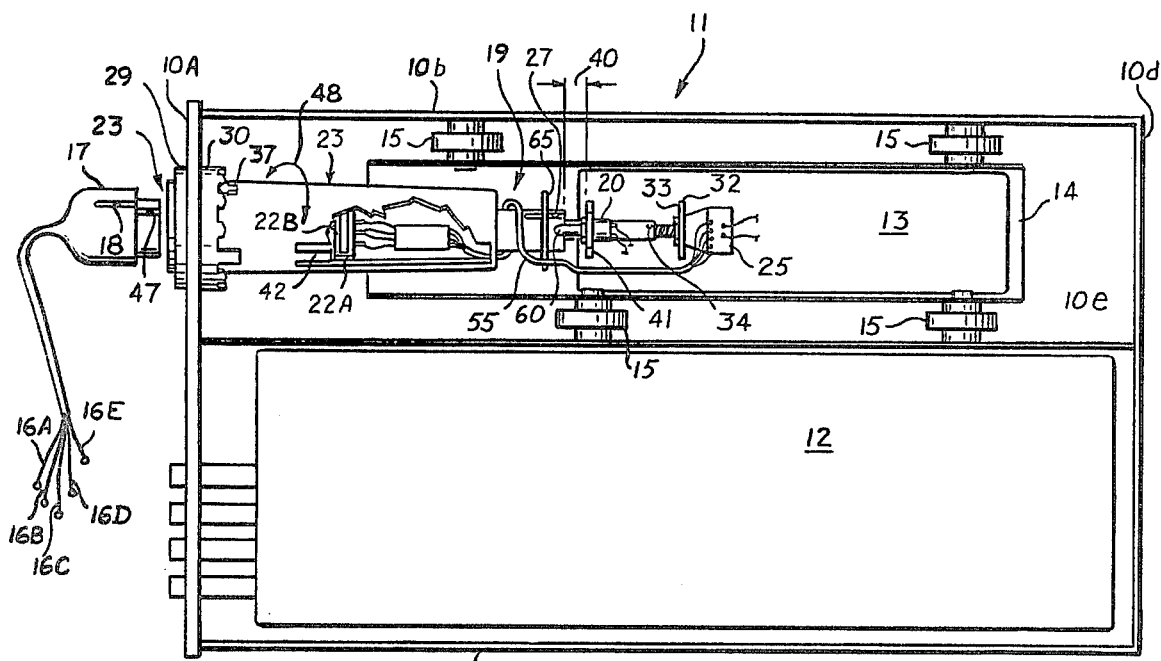
FIG. 2 is underside view of the signal processing apparatus of FIG. 1 partly broken away, showing combination input connector and lead selection switch and additionally a calibration switch of the invention in greater detail.
Figure 3:
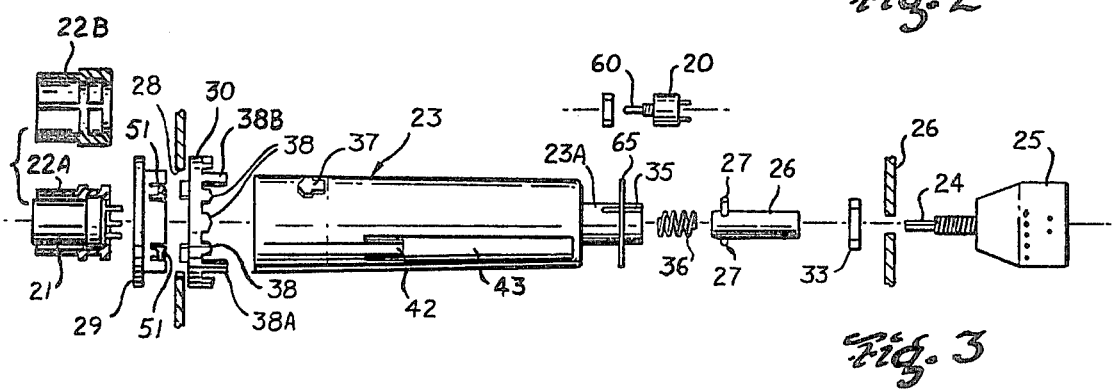
FIG. 3 is an exploded view of the components of FIG. 2 comprising the invention.

Referring to FIGS. 1-3, there is illustrated in FIG. 1 the front panel 10A of electrical signal processing apparatus such as a heart signal or ECG amplifier generally designated 11. The ECG amplifier 11 is contained within a housing comprised of front panel 10A, side panels 10B and 10C, and rear panel 10D, seen in the FIG. 2 underside view of amplifier 11. A surrounding cover (not shown) may serve to further enclose the circuitry of the apparatus. Typically the ECG amplifier 11 includes amplifier circuitry, generally represented as 12, which receives a preamplified heart signal from the preamplifier generally represented as 13. Preamplifier 13 may comprise a printed circuit board containing preamplifier circuitry of known design. The preamplifier 13 is rigidly but removably mounted within a metallic shielding channel 14 in turn supported in fixed spaced insulated relationship with housing wall 10B and partition 10E by means of insulating standoff supports 15. An inductive coupling (not shown) between preamplifier 13 of amplifier 12 serves to connect the output of the former to the input of the latter while maintaining electrical isolation therebetween.

The electrical heart signals which comprise the input to the preamplifier 13 are typically developed across various pairs of a plurality of input leads (here five) 16A, 16B, 16C, 16D and 16E. The respective leads 16A–16E may be connected through their respective electrodes in various known configurations to various locations on a patient's arms and/or legs and/or chest. The electrical potential between any selected pair of leads may then comprise the signal for input to preamplifier 13. The leads 16A–16E are connected to five respective male contacts fixedly positioned and spaced relative to one another within a connector plug 17. Plug 17 may be any one of a variety of conventional connector plug, preferably circular in cross section and of sufficient rigidity and longitudinal extent to facilitate insertion of the plug into a corresponding receiving connector and permit rotation thereof in accordance with the invention. Plug 17 additionally includes a longitudinally extending key 18 on the exterior surface thereof for the purpose to be hereinafter described.

The signal developed across any selected pair of leads 16A–16E is extended to the input of preamplifier 13 via the consolidated or combined input connector and lead selection switch of the invention, generally designated 19 and hereinafter referred to as CICLSS. The CICLSS 19, by consolidating the lead selection switch with the input connector, reduces the area on front panel 10A required for both functions. Additionally, the CICLSS 19 provides for the actuation of a calibration switch 20 without requiring additional space on front panel 10A for a separate calibration switch. Inasmuch as the front panel 10A also is required to mount other input lead connectors and various indicators and control knobs and buttons, including some which combine a rotary potentiometer with a push button switch, the consolidated structure of CICLSS 19 is particularly advantageous. The advantage of this consolidated structure is further realized in view of the increase emphasis placed on electrically isolating a patient from possible dangerous leakage current. Such isolation normally occurs intermediate the preamplifier 13 and the amplifier 12 and of course includes the functions of CICLSS 19 and also the calibration function provided by calibration switch 20.

Referring now to CICLSS 19 in greater detail, a connector receptacle 21 of conventional design adapted to receive connector plug 17 is housed within separable connector shell halves 22A and 22B in non-moving relationship therewith. The connector shell 22A, 22B is in turn removably housed within a forward portion of a molded plastic shaft or tube 23 in substantially fixed relationship therewith. The tube 23, in addition to housing the female connector 21 also serves to transmit switching torque to the input shaft 24 of a multi-position, multi-contact rotary selector switch 25 via a drive connection such as drive rod 26 having dog 27.

Accordingly, tube 23 is mounted in amplifier 11 for selectively rotatable and axially reciprocable movement respectively about and along an axis substantially coaxial with a generally circular opening 28 in the front panel 10A. Tube 23 is slidably and rotatably journaled at its front end within the inner bearings surface of an annular bezel 29 which is removably mounted in opening 28 in fixed relation with front panel 10A. An annular detent locking ring 30 removably engages the front panel 10A in non-rotating co-axial relationship with opening 28 and separably interlocks with bezel 29 for mounting the bezel in panel 10A.

Selector switch 25 is mounted to mounting bracket 32 by means of nut 33 which threadedly engages the threaded portion of the switch. Bracket 32 is in turn normally rigidly mounted to channel 14 (by means not shown) for fixedly positioning switch 25 within amplifier 11. Switch 25 is mounted such that its rotary input shaft 24 extends forwardly therefrom in co-axial relation with tube 23. The drive rod 26 includes a bore in the rear end thereof for receiving the switch input shaft 24 therewithin a relatively close fitting engagement. One or more set screws 34 in threaded engagement with drive rod 26 coact with input shaft 24, or a flat on shaft 24, to prevent relative rotational movement therebetween. Set screw 34 may also be used to prevent relative axial motion between drive rod 26 and input shaft 24. Alternatively, set screw 34 might be omitted and the bore in the rear end of drive rod 26 may be formed to include a flat for matching the flat on input shaft 24.

The forward end of drive rod 26 is slidably received within the rearward end portion 23A of tube 23. Rear end portion 23A is a smaller outside and inside diameter than the remaining forward portion of tube 23 and is separated therefrom by a septum 31 therebetween. The overall length of tube 23 may be about 5 inches with rear portion 23A comprising about one inch thereof. A pair of axially extending slots 35 through the walls of tube rear portion 23A on opposite sides thereof extend forwardly from the rear end of tube 23 for about one-half inch along rear portion 23A. Slots 35 slidingly receive a respective pair of dogs 27 extending radially outward from diametrically opposite sides of drive rod 26 for transmitting torque from tube 23 to drive rod 26 and subsequently input shaft 24. A compression spring 36 is housed within the rearward tube portion 23A and acts in opposition against the spring seat defined by tube septum 31 and the forward end face of drive rod 26 to generally bias tube 23 forwardly to a detented limit position to be hereinafter described. Similarly, this rearwardly directed force of spring 36 may act to maintain drive rod 26 in substantially constant axially abutting engagement with the threaded stem on selector switch 25, particularly if set screw 34 is omitted or not capable of preventing relative axial movement. The width or angular extent of the slots 35 is only slightly greater than the width or diameter of dogs 27 to closely restrict the relative angular freedom therebetween such that a selected angle of rotation of tube 23 result in substantially the same angle of rotation of switch input shaft 24.

A generally arrow-shaped stop or detent finger 37 is affixed to the outer surface of tube 23 near the forward end thereof, as by integral molding therewith. The detent locking ring 30 includes a number of castellations 38, 38A and 38B, extend rearwardly from the circumference of locking ring 30 in angularly spaced relation with one another to create respective interdental spaces therebetween. Castellations 38 extend rearwardly from their respective roots for a lesser distance than the two longer castellations 38A, 38B (for instance $\frac{1}{8}''$ vs. $\frac{1}{2}''$). The interdental spacing between adjacent castellations 38, 38A, 38B and the size and the shape of detent finger 37 are selected such that finger 37 may move forwardly into a selected interdental space in captive relation between a pair of respective adjacent castellations 38 (or also 38A or 38B). More specifically the detent finger 37 may take the shape of a forwardly directed arrowhead such that the inwardly inclined opposite sides of the "arrowhead" serve as caming surfaces for facilitating the seating and centering of finger 37 within a selected interdental space. The angle on the detent finger "arrowhead" 37 may be selected such that the "point" or apex of the arrowhead contacts the detent ring 30 to limit the forward travel of tube 23 when retained in detented engagement between adjacent castellations. It will be appreciated that the angular spacing between the centers of successive interdental spaces will correspond with the angular extend to which switch input shaft 24 must be rotated between each successive switch contact position. In the illustrated embodiment, switch 25 may have four or more possible switch positions, however, only four combinations of leads 16A–16E are required such that only four positions of the switch 25 are used. Accordingly, it is preferable that detent ring 30 limit the selected detented angular positionings of tube 23 to those four positions corresponding with the respective four angular inputs from switch input shaft 24.

For this reason, castellations 38A and 38B extend rearwardly a substantially greater distance than castellations 38 to limit the angular rotation of tube 23 and are themselves angularly spaced such as to include three castellations 38 and the respective four interdental spaces therebetween. It will be appreciated that detent finger 37 is normally biased forward into detented engagement with ring 30 and that rearward displacement of tube 23 will enable it and its detent finger 37 to be rotated to any of the four interdental spaces between castellations 38A and 38B. The length of castellations 38A and 38B are selected to be greater than the maximum possible rearward displacement of tube 23, as indicated by arrow 40 and generally determined by the actual spacing between the rear face of tube 23A and a calibration switch bracket 41 as will be described hereinafter in greater detail. Accordingly, the maximum possible axial displacement 40 of tube 23 is greater than the axial extent of castellations 38 but less than the axial extent of castellations 38A and 38B which comprise angular stops.

With the foregoing arrangement, the stop-castellations 38A 38B embrace four interdental spaces, however, it will be appreciated that there remain another eight interdental spaces about the circumference beyond those stops. Accordingly, by either remounting detent ring 30 in a different angular configuration or alternatively having a rotary switch differently oriented angularly relative to bracket 32, the alternative range having eight interdental spaces becomes available for use.

The female connector 21 has generally cylindrical form and includes a radially enlarged shoulder near its rearward end. Similarly, the connector housing shell halves 22A, 22B, each include a shoulder-receiving portion structured to axially and radially restrain connector 21 when the shell halves are placed therearound. Further, the shoulder-receiving section of shell-half 22B includes an axially-extending key on the inner surface thereof for mating engagement with a complimentary keyway formed in the shoulder of the female connector 21 to prevent relative rotation therebetween.

The inside diameter of the forward end of tube 23 is sized to receive connector shell halves 22A, 22B with female connector 21 therewithin. A pair of snap-lock fingers 41 integrally formed in tube 23 extend rearwardly within respective elongated slots 43 on opposite sides of the tube. Raised ridges 44 extending longitudinally of the inner surface of tube 23 along its mid-section create axially-facing stop surfaces at their forward end for axially abutting engagement with the rear face of connector shells 22A, 22B. The size and spacing of the shoulders of connector shells 22A, 22B, snap-lock fingers 42 and the raised ridges 44 are such that shells 22A, 22B are removably retained in constant axialy positioning within tube 23. Moreover, an axially extending key 45 in the outer surface of connector shell half 22B is received in the longitudinally extending key way 46 in the inner surface of tube 23 to prevent relative rotation therebetween.

The key 18 on the outer surface of plug 17 also is received in the key way 46 in tube 23 to prevent relative rotation therebetween and a keyway 47 in an extension of plug 17 receives the axially extending key in connector shell half 22B for a similar purpose. In this way, the substantially rigid plug 17, when connected with female connector 21, may be forced inwardly (rearward) to disengage detent finger 37 from locking ring 30 and subsequently rotated, as indicated by arrows 48 to a selected switch position. Removal of the rearward force on plug 17 enables compression spring 36 to force tube 23 forward and its detent finger 37 into the interdental space associated with the selected switch positioning. A slot 49 in the forward-most end of tube 23 and aligned with key way 46 and detent finger 37 serves, with key way 46, as a visual indicator of the rotational or angular orientation of tube 23. Appropriate indicia on an annular indicator member 50 for selecting particular switch positions.

As previously noted, the bezel 29 and detent locking ring 30 removable interlockingly engage one another to effect their respective mountings at front panel 10A. More specifically, referring to FIG. 9, annular bezel 29 includes a radially enlarged shoulder portion 29A at its forward end of larger diameter than opening 28 in panel 10A. The tube bearing inner surface of bezel 29 comprises a short cylindrical segment extending rearwardly from shoulder 29A and sized for closefitting insertion within the opening 28. This tube bearing surface portion of bezel 29 includes four rearwardly extending snap-locks 51 equiangularly spaced about the bezel and adapted for axially and radially engaging and retaining the detent locking ring 30 inserted thereover.

Detent locking ring 30 includes radially-recessed snap-lock seats 52 around the inner surface thereof in the interdental spaces between each of the castellations 38, 38A and 38B. Although a total of twelve snap-lock seats 52 exist in the snap-lock ring 30 of the illustrated embodiment, only four are required for engagement by snap-locks 51 of the bezel 29. However such arrangement permits other possible rotational relationships between bezel 29 and detent ring 30 in the event the eight-position switching range of the locking ring is to be utilized. The angular or rotational orientation of locking ring 30 (and thus bezel 29) relative to front panel 10A is determined and maintained by four locating stubs 53 equiangularly located about ring 30 and extending forwardly thereof into four respective holes (not shown) in front panel 10A. These small holes in panel 10A are equiangularly located about central openings 28 and are sized to closely engage locating stubs 53 to prevent rotational movement of ring 30. The outside diameter of ring 30 is of course greater than the diameter of the front panel opening 28 and the length of bezel snap-locks 51 and the location of snap-lock seat 52 are such that bezel 29 and detent locking ring 30 are positioned in close, opposing relationship on opposite sides of front panel 10A when in interlocking engagement with one another.

The five leads 16A-16E are extended, via five respective male contacts in plug 17, to five corresponding female contacts in connector receptacle 21 which in turn provides five output contacts or terminals at its rearward end for direct or indirect connection with five respective input terminals on selector switch 25. In the illustrated embodiment, a small circuitboard containing radio frequency circuitry is housed within tube 23 rearwardly of connector 21 and shells 22A, 22B. The five leads from the rearward end of connector 21 are connected to an input side of the radio frequency suppression circuitry, the output of which is extended over five respective leads contained within cable 55 to the five respective input contacts on selector switch 25. Conductor cable 55 exits from the interior of tube 23 through a small slot 56 in the intermediate rear end face of tube 23 radially outward of septum 31.

According to another aspect of the present invention, calibration of the amplifier input may be effected by actuation of calibration switch 20 mounted on bracket 41. Calibration switch 20 is a push button microswitch, mounted with the pubh-button actuator 60 extending forwardly to be contacted by an actuating ring 65 integrally moulded on the rear tube portion 23A. Calibration switch bracket 41 is rigidly mounted (by means not shown) to channel 14 and positions switch 20 such that rearward movement of tube 23 moves actuator ring 65 into actuating contact with push button actuator 60. More specifically, in the illustrated embodiment, the relative spacing of actuator ring 65 from the rear end face of rear tube portion 23A and the spacing of that end face from the switch support bracket 41 are preselected such that the bracket limits rearward movement of tube 23 to only that necessary for actuation of switch 20. Such arrangement prevents the inadvertent applying of excessive force to the push button actuator 60. Further to this end, the actuator ring 65 is mildly resilient and push-button actuator 60 is positioned sufficiently radially outward from the axis of tube 23 to contact ring 65 near its outer edge. This permits slight forward deflection of the actuator ring 65 if the opposing force between it and switch actuator 60 becomes excessive. As previously noted, the maximum axial displacement of tube 23 is indicated by arrows 40 and is now seen to be determined by the spacing between the rear end of tube 23 and the switch bracket 41.

Although the foregoing description of the element for housing the female connector 21 and serving to transmit torsional and axial forces to switches 25 and 20 respectively was described as being a tube 23, it should be understood the term "tube" is intended to embrace any functionally similar shaft-like structure capable of operating in the manner previously described. Accordingly, tube 23 would not necessarily require a circular cross section throughout its entire length, nor would it need to be hollow throughout most of its entirely, nor would it require that the connector-housing forward portion be of larger cross sectional area than the rearward spring seating and dog engaging portions of 23A.

The invention may be embodied in other specific forms without departing from spirit or essential characteristic thereof. The present embodiments are therefor to be considered in all respects as illustrative and not restrictive, the scope of the invention being indicated by the appended claims rather than by the foregoing description, and all changes which come within the meaning and range of equivalency of the claims and therefore intended to be embraced therein.

What is claimed is:

1. For electrical signal input to signal processing apparatus having a housing including a panel, a combined input connector and lead selection switch adapted for connection with a first-half of a multi-contact connector for plural input signal leads, said combination being mountable in said apparatus housing at least partially in registry with an opening through said panel, and comprising:

a multi-position rotary switch having a plurality of input terminals, at least one output terminal and an input shaft, said switch input shaft being rotatable to plural discrete positions for respectively changing the connection between said switch input terminals and said at least one switch output terminal, said switch being adapted to be substantially fixedly mounted in said apparatus housing;

a second half of said multi-contact connector adapted to removably receive said first half of said multi-contact connector for electrical connection with the plural input signal leads;

means for electrically connecting the contacts of said second half of said multi-contact connector with respective ones of said switch input terminals;

connector-receiving means mounted in said apparatus housing in registry with the opening in said apparatus panel for retainedly housing said second half of said multi-contact connector and for detented rotation to plural selected angular positions about an axis of rotation extending substantially normal to said apparatus panel, said connector-receiving means having a substantially rigid shaft member, at last part ot said shaft member extending rearwardly from said panel into said apparatus housing, said shaft member being axially hollow at its forward end and retaining said multi-contact connector second half therewithin; and drive means connecting said connector-receiving means with said input shaft of said rotary switch whereby said selective rotation of said connector-receiving means is operative to selectively change the connection between said switch input terminals and said at least one switch output terminal.

2. The combined input connector and lead selection switch of claim 1 including means connecting said multi-contact connector second half to said shaft member against relative rotation therebetween whereby rotation of said connector second half is operative to actuate said rotary switch.

3. The combined input connector and lead selection switch of claim 2 including a multi-piece housing for substantially fixedly retaining said multi-contact connector second half therewithin and said shaft member includes means for releasably retaining said multi-piece housing therewithin.

4. The combined input connector and lead selection switch of claim 3 wherein said shaft member has stop means therewithin for limiting the rearward positioning of said multi-piece housing therewithin, said multi-piece housing includes a radially extending shoulder presenting a forwardly facing contact surface, and said means for releasably retaining said multi-piece housing within said tube comprises resilient locking finger means extending radially inwardly from the inside diameter of said shaft member in axially opposed relation with said shoulder of said multi-piece housing for axially retaining said multi-piece housing and being resiliently radially displaceable therefrom for selective insertion and removal of said multi-piece housing.

5. The combined input connector and lead selection switch of claim 3 wherein said multi-piece housing and said shaft member each include manually cooperating means for preventing relative rotation therebetween and said multi-contact connector second half and said multi-piece housing each include mutually cooperating means for preventing relative rotation therebetween.

6. The combined input connector and lead selection switch of claim 1 wherein said shaft member is selectively movable normally of said panel between forward and rearward positions, biasing means operatively coact between said shaft member and said apparatus housing for urging said shaft member to said forward position, and said connector-receiving means includes detent means for normally preventing rotation of said shaft member relative to said panel and housing when said shaft member is in said forward position and for allowing said relative rotation between said shaft member and said housing when said biasing means is overcome and said member is moved to said rearward position.

7. The combined input connector and lead selection switch of claim 6 wherein said detent means comprises a first detent member mounted on said housing against angular displacement about the axis of rotation of said shaft member and a second detent member mounted on said shaft member against angular displacement relative thereto.

8. The combined input connector and lead selection switch of claim 7 wherein said first detent member comprises a castellated locking ring mounted on said panel in coaxially encircling relationship with said shaft member, the castellations comprising a series of axially extending teeth in angularly-spaced relation with one another around said axis of rotation and said second detent member comprises a finger for detented engagement with said locking ring within the interdental spaces between adjoining castellations.

9. The combined input connector and lead selection switch of claim 8 wherein said first and second detent members additionally coact axially to limit forward sliding movement of said shaft member and thereby determine said forward position thereof.

10. The combined input connector and lead selection switch of claim 9 wherein two of said castellations respectively at opposite ends of a predetermined range of angular operability of said shaft member extend rearwardly of said panel a greater distance than the other castellations therebetween sufficient to prevent rotation of said second detent member therebeyond when said shaft member is in its said rearward position.

11. The combined input connector and lead selection switch of claim 6 wherein said input shaft of said rotary switch and said shaft member are substantially coaxial, said shaft member is axially hollow at its rearward end and includes at least one axially extending slot in the wall thereof, and said drive means comprises a rigid elongated member adapted at one end thereof for relatively non-rotating connection with said input shaft of said rotary switch, the other end of said elongated member extending slidably into said hollow at the rearward end of said shaft member and having dog means extending radially outward therefrom through said at least one slot in the wall of said shaft member whereby said dog means is angularly engaged for rotating said rotary switch input shaft when said shaft member is rotated.

12. The combined input connector and lead selection switch of claim 11 wherein said biasing means comprises a coil spring, said hollow at the rearward end of said shaft member includes spring seating means, and said coil spring is positioned intermediate said spring seating means and said elongated member in compressed, axially opposing engagement therewith.

13. The combined input connector and lead selection switch of claim 6 additionally including linearly-actuated other switch means substantially fixedly mounted in said apparatus housing and having an actuator member movable between forward and rearward positions relative to said apparatus housing panel for changing the conduction state of said other switch, and said shaft member includes means affixed thereto for moving said other switch actuator member between said forward and rearward positions thereof in response to forward and rearward positioning of said shaft member respectively at a plurality of said plural selected angular positions thereof.

14. The combined input connector and lead selection switch of claim 13 wherein said actuator member of said other switch means is linearly actuated and is biased to its said forward position, and said actuator-member moving means affixed to said shaft member is slightly yieldable in the axial direction thereby to prevent excessive force on said actuator member of said other switch means when said tubular member is moved to its rearward position.

15. The combined input connector and lead selection switch of claim 13 wherein the signal processing apparatus includes electrical calibration means and said other switch means controls operations of said calibration means.

16. The combined input connector and lead selection switch of claim 8 additionally including linearly-actuated other switch means substantially fixedly mounted in said apparatus housing and having an actuator member movable between forward and rearward positions relative to said apparatus housing panel for changing the conduction state of said other switch, and said shaft member includes means affixed thereto for moving said other switch actuator member between said forward and rearward positions thereof in response to forward and rearward positioning of said shaft member respectively at a plurality of said plural selected angular positions thereof.

17. The combined input connector and lead selection switch of claim 12 additionally including linearly-actuated other switch means substantially fixedly mounted in said apparatus housing and having an actuator member movable between forward and rearward positions relative to said apparatus housing panel for changing the conduction state of said other switch, and said shaft member includes means affixed thereto for moving said other switch actuator member between said forward and rearward positions thereof in response to forward and rearward positioning of said shaft member respectively at a plurality of said plural selected angular positions thereof.

* * * * *